United States Patent [19]
Johnston et al.

[11] Patent Number: 5,843,153
[45] Date of Patent: Dec. 1, 1998

[54] STEERABLE ENDOCARDIAL LEAD USING MAGNETOSTRICTIVE MATERIAL AND A MAGNETIC FIELD

[75] Inventors: Matthew M. Johnston; Steven R. Conger, both of Angleton, Tex.

[73] Assignee: Sulzer Intermedics Inc., Angleton, Tex.

[21] Appl. No.: 893,279

[22] Filed: Jul. 15, 1997

[51] Int. Cl.$^6$ .................................................. A61M 25/01
[52] U.S. Cl. ............................................ 607/122; 600/585
[58] Field of Search ............................ 600/585; 607/122, 607/125

[56] References Cited

U.S. PATENT DOCUMENTS

| | | |
|---|---|---|
| 3,043,309 | 7/1962 | McCarthy . |
| 3,358,676 | 12/1967 | Frei et al. . |
| 3,769,984 | 11/1973 | Muench . |
| 4,063,561 | 12/1977 | McKenna . |
| 4,244,362 | 1/1981 | Anderson .................................. 600/585 |
| 4,809,713 | 3/1989 | Grayzel . |
| 4,944,727 | 7/1990 | McCoy . |
| 5,055,101 | 10/1991 | McCoy . |
| 5,090,956 | 2/1992 | McCoy . |
| 5,129,404 | 7/1992 | Spehr et al. . |
| 5,257,636 | 11/1993 | White . |
| 5,353,807 | 10/1994 | DeMarco ................................. 600/585 |
| 5,431,640 | 7/1995 | Gabriel . |
| 5,449,369 | 9/1995 | Imran . |

FOREIGN PATENT DOCUMENTS

| | | |
|---|---|---|
| 40 14 947 | 11/1991 | Germany . |
| 42 15 901 | 8/1993 | Germany . |

Primary Examiner—William E. Kamm
Assistant Examiner—Carl H. Layno
Attorney, Agent, or Firm—John R. Merkling

[57] ABSTRACT

Magnetically alterable material, such as magnetostrictive material, is used in combination with a suitable substrate and a suitable magnetic field to produce a stylet and lead assembly that curves in response to a suitable magnetic field.

15 Claims, 6 Drawing Sheets

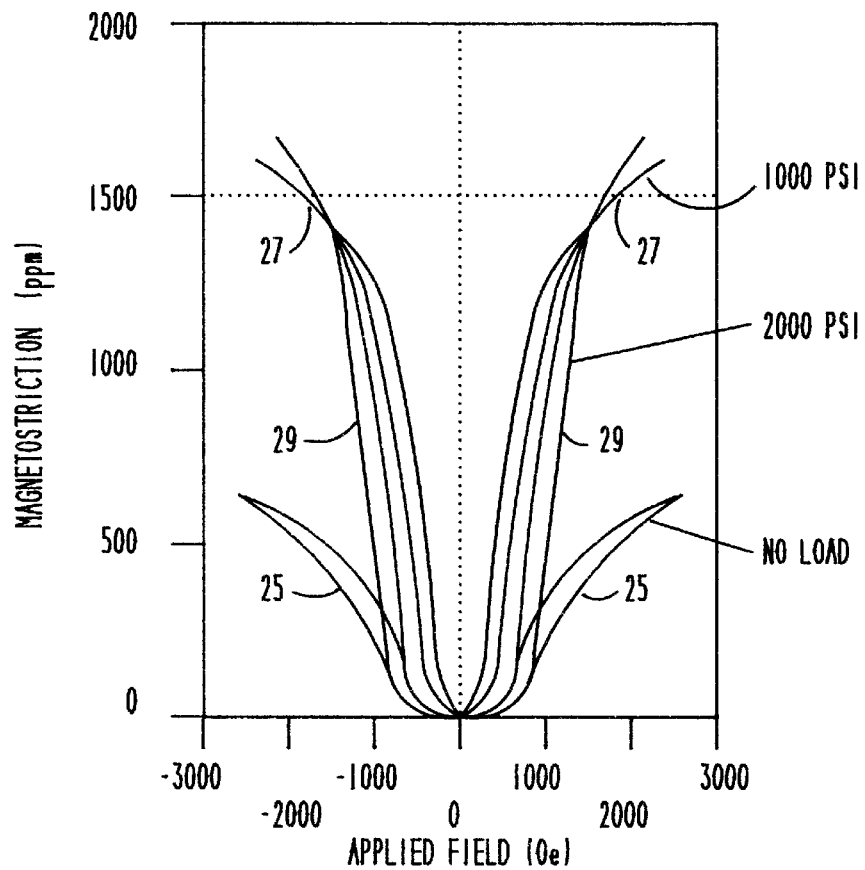
FIG. 5
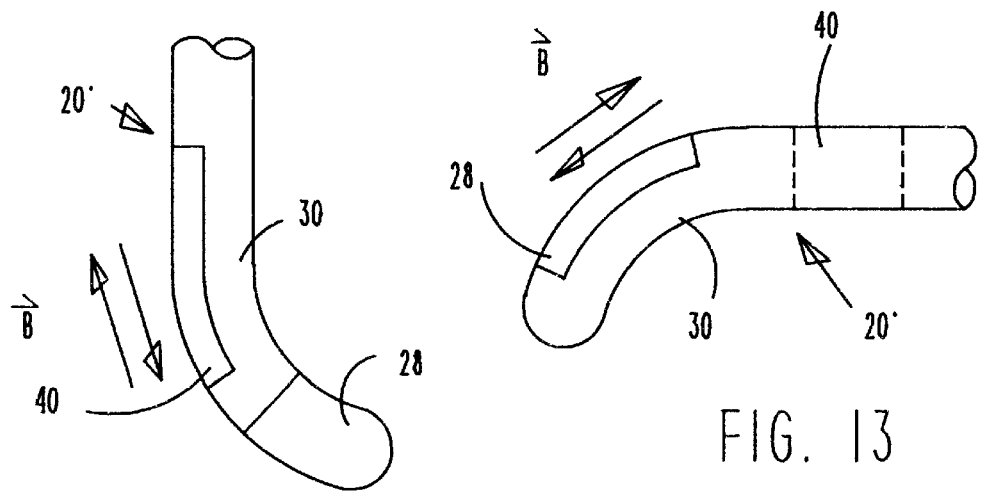
FIG. 12
FIG. 13

STEERABLE ENDOCARDIAL LEAD USING MAGNETOSTRICTIVE MATERIAL AND A MAGNETIC FIELD

BACKGROUND OF THE INVENTION

1. Field of the Invention

The present invention relates generally to cardiac stimulation and, more particularly, to an implantable endocardial lead assembly with apparatus for magnetically steering the lead assembly during implantation.

2. Description of the Related Art

For a variety of reasons, a person's heart may not function properly and, thus, endanger the person's well-being. Medical devices have been developed to facilitate heart function. For instance, if a person's heart does not beat properly, a cardiac stimulator may be used to provide relief. A cardiac stimulator, such as a pacemaker, is a medical device that delivers electrical stimulation to a patient's heart. A cardiac stimulator generally includes a pulse generator for creating electrical stimulation pulses and at least one conductive lead having an electrode at one end for delivering these electrical stimulation pulses to the designated portion of the heart.

Dual chamber pacemakers are capable of sensing and/or pacing in two chambers, typically the right atrium and right ventricle. Accordingly, dual chamber pacemakers typically utilize two leads—an atrial lead and a ventricular lead. The distal ends of the atrial lead and the ventricular lead are coupled to the dual chamber pacemaker. The proximal end of the atrial lead is threaded through the superior vena cava and into the right atrium of the heart. Similarly, the proximal end of the ventricular lead is threaded through the superior vena cava, through the right atrium, and into the right ventricle of the heart. Each lead includes a mechanism on its distal end that attaches to the inner wall of the heart to establish the required electrical connection between the pacemaker and the heart.

Since leads of this type reside within a beating heart, the heart imparts mechanical forces into the leads almost constantly. Such forces cause the leads to bend and flex over and over again. Because of this somewhat severe environment, such leads are typcially made to be quite flexible to withstand these forces for a prolonged period of time. By way of example, a lead may include a coiled conductor covered in polyurethane to provide the desired flexibility.

To implant a lead, a physician inserts the lead through a body vessel, such as a vein or an artery, and, using fluoroscopy, directs the lead into the heart. However, because the lead is so flexible, it cannot typically be directed through the body vessel and into the heart without some means of guiding the lead through complex vasculature. Common leads are hollow along their length. Therefore, the physician typically guides the lead into the patient's heart by manipulating a stylet that is disposed within the lead. A common stylet is stiffer than a lead, yet flexible enough to wind through the body vessels and heart chambers. Once the physician places the lead's electrode at the proper location within the heart, the physician withdraws the stylet from the lead.

In many cases, the precise placement of the lead's electrode within the heart is desirable. Conventional techniques for guiding the electrode to the desired location in the heart place great reliance on the skill of the physician in preforming and manipulating the stylet to position the electrode accurately. When a physician encounters obstructions or irregularities in the body vessels or heart of the patient, the physician must often repeatedly withdraw, reform, and advance the lead assembly until the distal end of the lead assembly is able to pass the obstruction. Because the electrode is located at the distal end of the relatively flexible lead assembly, there is often some trial and error associated with positioning the electrode next to the desired region of the myocardium.

A more automated procedure for locating a lead's electrode involves application of an external magnetic field to the patient's body to interact with a permanent magnet fixed to the lead. A hand held permanent magnet is passed over the patient's body in the vicinity of the electrode during implantation. The magnetic field associated with the hand held magnetic either propels or attracts the permanent magnetic in the lead. In either case, the lead can only be moved along a single line directly toward or directly away from the control magnet. As a consequence, such permanent magnet systems provide only crude directional control and require a rather high level of skill to locate the electrode accurately.

The present invention is directed to overcoming, or at least reducing the effects of, one or more of the aforementioned disadvantages.

SUMMARY OF THE INVENTION

In accordance with one aspect of the present invention, there is provided a stylet. The stylet includes a first member and a second member that is coupled to the first member. The second member is a magnetostrictive material.

In accordance with another aspect of the present invention, there is provided an stylet that includes a first elongated member and a second elongated member. The second elongated member is coupled longitudinally to the first elongated member. The second elongated member is a magnetostrictive material.

In accordance with another aspect of the present invention, there is provided a lead assembly for implantation in a patient. The lead assembly includes a lead adapted to transmit electrical impulses. A first member is coupled to the lead. A second member is coupled to the first member. The second member is made of a magnetostrictive material.

BRIEF DESCRIPTION OF THE DRAWINGS

Certain advantages of the invention may become apparent upon reading the following detailed description of exemplary embodiments of the invention and upon reference to the drawings in which:

FIG. 5 is a graph representing magnetostrictive strength versus strength of an applied magnetic field for various loads;

FIG. 12 is a top view of the stylet of FIG. 9 under the influence of one of two opposing magnetic fields;

FIG. 13 is a side view of FIG. 12 showing the influence of one of two opposing magnetic fields;

DETAILED DESCRIPTION OF SPECIFIC EMBODIMENTS

Figure 1:
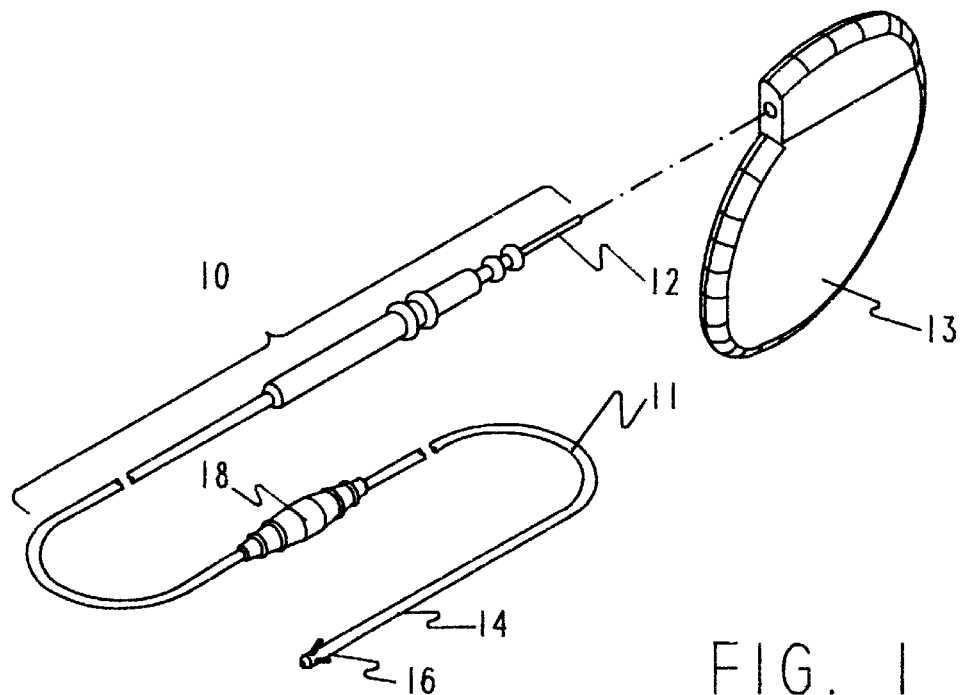
FIG. 1 is a perspective view of an implantable endocardial lead assembly in accordance with the present invention.

Turning now to the drawings, and referring initially to FIG. 1, an endocardial lead assembly is illustrated and generally designated by a reference numeral 10. The lead assembly 10 is designed to be inserted through a body vessel, such as the jugular vein, directly into the body for diagnostic or therapeutic purposes. The lead assembly 10 includes a lead body 11 that has a proximal end 12 that may be coupled to a cardiac stimulation device 13, such as, for example, a pacemaker or cardioverter/defibrillator. The distal end 14 of the lead body 11 is attached to an electrode assembly 16. A suture sleeve 18 is slidably disposed on the lead body 11. The suture sleeve 18 may be attached to the insertion vessel of a patient in a conventional manner.

Figure 2:
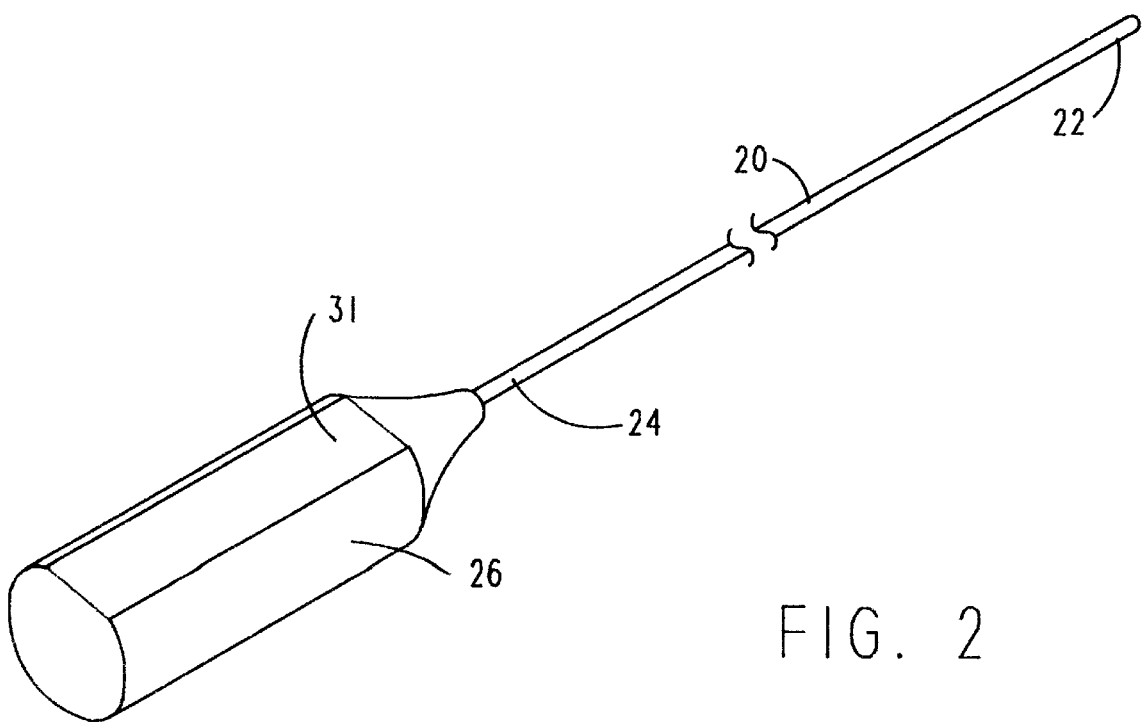
FIG. 2 illustrates a steerable stylet and handle in accordance with the present invention.

To implant the lead assembly 10, a stylet, which is relatively stiff in comparison with the flexible lead assembly 10, is disposed within the lumen of the lead body 11. Referring to FIG. 2, one embodiment of a stylet is illustrated and generally designated by a reference numeral 20. The stylet 20 includes a distal end 22 that is normally disposed within the lead body 11 at or near the distal end 14 of the lead body 11. The proximal end 24 of the stylet 20 projects from the proximal end 12 of the lead body 11. A physician controls the longitudinal and rotational movement of the stylet 20 by using a handle 26 that is coupled to the proximal end 24 of the stylet 20.

With the stylet 20 disposed within the lead assembly 10, a physician may insert the lead assembly 10 into a body vessel of a patient and guide the lead assembly 10 into its proper position. As can be appreciated, body vessels tend to curve and flex. Accordingly, the stylet 20 is flexible enough to conform to the shape of a body vessel, yet it is stiff enough to guide the lead assembly 10 through the body vessel. Thus, when the stylet 20 is inside a body vessel, the stylet 20 typically takes on the curved shape of the body vessel, and, in the context of this discussion, these curves of the stylet 20 are referred to as "conformal curves."

To facilitate the ability of the stylet 20 to guide the lead assembly 10 through a body vessel, the stylet 20 may be non-conformally curved in situ. In other words, while the stylet 20 resides within a body vessel, the stylet 20 may be non-conformally curved by a stimulus other than the force imparted to the stylet 20 by the body vessel to produce a conformal curve. By having the ability to curve the stylet 20 in a desired direction during the implantation process, a physician may be better able to guide the stylet 20 through a curved or obstructed body vessel.

Figure 3:
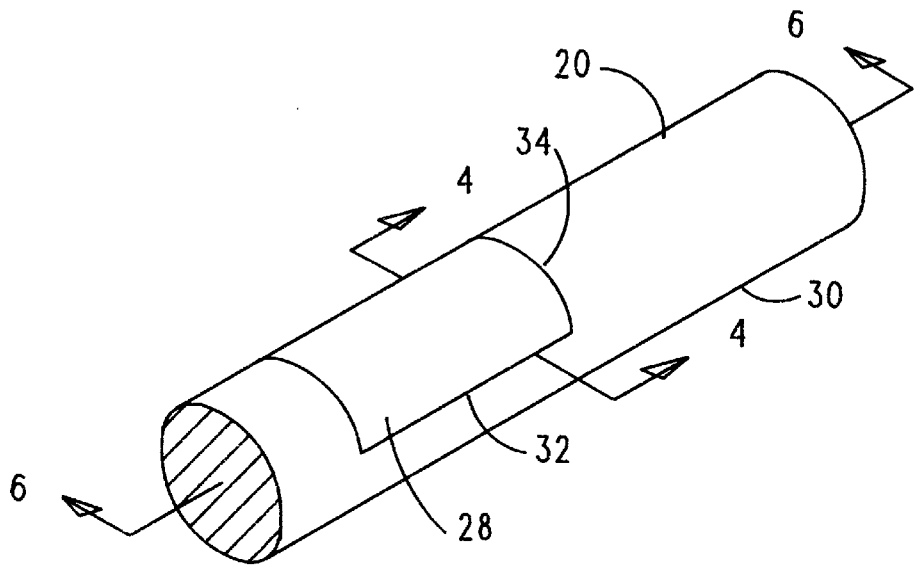
FIG. 3 is a perspective view of a portion of the steerable stylet of FIG. 2.
Figure 4:
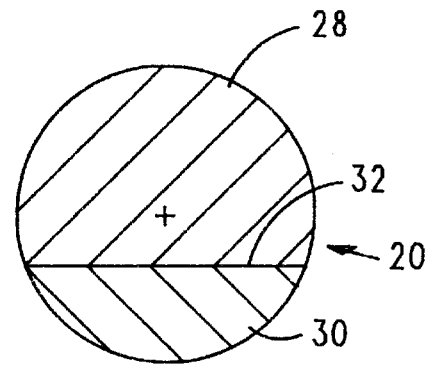
FIG. 4 is a cross-sectional view the stylet taken at line 4—4 in FIG. 3.

To give the stylet 20 the ability to be non-conformally curved, the stylet 20 uses at least two elements coupled together. At least one of these elements is capable of movement to produce a desired curvature in the stylet 20. FIGS. 3 and 4 illustrate one exemplary embodiment of the stylet 20. In this embodiment, the stylet 20 includes two material members 28 and 30 coupled together along at least a portion of the stylet 20. The member 28 is advantageously composed of a magnetostrictive material. The other member 30 is advantageously composed of a substrate material that is relatively non-magnetostrictive as compared with the member 28. Because magnetostrictive materials change length in response to the application of a magnetic field, the magnetostrictive member 28 will elongate in the presence of a suitable magnetic field. The magnetic field does not cause the substrate member 30 to change shape substantially, so it essentially retains its original length. Therefore, in the presence of a suitable magnetic field, the change in length of the magnetostrictive member 28 relative to the substrate member 30 produces a curvature in the stylet 20. It should also be noted that the substrate member 30 may be made of a magnetostrictive material that has a response opposite the magnetostrictive member 28 to achieve a relative change in length between the two members 28 and 30 in response to the presence of a suitable magnetic field.

The type of deformation, e.g., elongation or contraction, depends upon the type of magnetostrictive material that is used. The magnitude of the change in length of the magnetostrictive member 28 depends upon the magnitude of the magnetic field applied axially to the magnetostrictive member 28 and upon the particular magnetostrictive material used. In this embodiment, the magnetostrictive member 28 is advantageously composed of TERFENOL-D available from Etrema Products, Inc., although other suitable types of magnetostrictive materials may also be used. The magnetostrictive material TERFENOL-D also exhibits inverse magnetostriction (known as the Villari effect), a phenomenon in which a change in magnetic induction occurs when a mechanical stress is applied along a specified direction to a material having magnetostrictive properties. These measurable changes in induction enable TERFENOL-D to be used in sensing applications (such as magnetotagging) where changes in stress occur. Consequently, the flexure of the device within the body can be sensed and used as a motion transducer for diagnostic purposes.

Examples of suitable materials for the substrate member 30 may include titanium, aluminum, magnesium, and stainless steel. As with the materials used to form virtually all stylets, the material used to fashion the substrate member 30 advantageously has a relatively high flexibility to facilitate the large and frequent bending movements associated with in vivo insertions.

FIGS. 3 and 4 show one possible combination of the members 28 and 30. Since the lead assembly 10 is typically cylindrical in shape, stylets are normally cylindrical in shape also. Accordingly, the members 28 and 30 are advantageously formed into a cylindrical shape. However, it should be recognized that other shapes may be suitable, so long as the stylet 20 is capable of being inserted into the lead assembly 10.

As illustrated in FIGS. 3 and 4, the members 28 and 30 are shaped as semi-cylindrical segments having a longitudinal interface 32 and a radial interface 34. The members 28 and 30 may be bonded together at the radial interface 34 and at least one point along the longitudinal interface 32. The members 28 and 30 may be adhesively bonded together using a suitable adhesive, such as Loctite 496 or Armco 631, although other suitable techniques, such as spot welding, hot coextrusion, or soldering, may also possibly be used.

The manner in which the members 28 and 30 are constructed may vary. One factor to be considered relates to the strength of the magnetostrictive member 28 during expansion or contraction. As illustrated in FIG. 5, the amount of magnetostriction of TERFENOL-D, measured in parts per million, varies depending upon the strength of the applied magnetic field, measured in Oerstads (Oe). The amount of magnetostriction also depends upon the initial load placed on the magnetostrictive material. As can be seen, the curves 25 illustrate relatively weak magnetostriction when no initial load is placed on the magnetostrictive material. However, as the curves 27 and 29 illustrate, the strength of magnetostriction increases when an initial preload of 1000 psi and 2000 psi, respectively, is placed on the magnetostrictive material. Accordingly, it may be desirable to place a preload on the magnetostrictive member 28 at the time it is coupled to the substrate member 30.

By way of example, a method for manufacturing a stylet 20 will be described with an initial preload in mind. First, it may be desirable to machine the magnetostrictive member 28 and the substrate member 30 to the proper sizes and configurations. For instance, if one or more magnetostrictive members 28 are to be placed at certain locations on the stylet 20, the magnetostrictive members 28 are cut and ground to the appropriate sizes. Similarly, slots for receiving the magnetostrictive members are formed in the substrate member 30. However, under certain circumstances, it may be desirable to couple the members 28 and 30 together first and machine the members 28 and 30 to a suitable size and configuration afterward.

To place a preload on the magnetostrictive member 28, the substrate member 30 is placed in a stretching device. The stretching device places a desired amount of tension on the substrate member 30. A suitable adhesive is applied to the substrate member 30, and the magnetostrictive member or members 28 are clamped to the substrate member 30. The clamped structure is cured, possibly in an oven, to complete the bonding process. Once cured, the tension is slowly released to prevent sudden stresses that may tend to delaminate the members 28 and 30. If the structure curls after the tension has been released, it may be desirable to bond it to another substrate (not shown) to provide additional strength to keep the stylet 20 relatively straight.

It is important to dispose the magnetostrictive members 28 in the correct direction to achieve the desired bending effect. Magnetostrictive material is polycrystalline. Thus, the molecular structure of magnetostrictive material is fairly well-ordered as compared to an amorphous material, but not as well-ordered as a truly crystalline material. For the magnetostrictive member 28 to elongate or contract in the longitudinal direction of the stylet 20, the polycrystalline molecules in the material should be generally perpendicular to the longitudinal surface of the substrate member 30.

Figure 6:
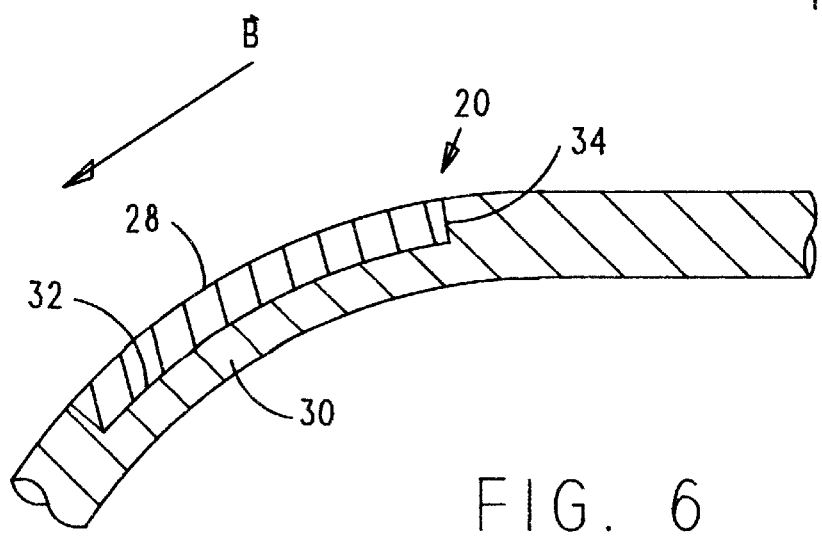
FIG. 6 is a side view of the stylet of FIG. 3 under the influence of one of two opposing magnetic fields.

FIG. 6 is a cross-sectional view taken along line 6—6 of FIG. 3 of the stylet 20 in the presence of a suitable magnetic field B. As can be seen, the magnetic field B causes the magnetostrictive member 28 to increase in length. The increase in the length of the magnetostrictive member 28 is exaggerated as shown in FIG. 6 for illustration purposes.

The point or points along the interface 32 where the members 28 and 30 are bonded impact the radius of curvature of the stylet 20. For example, if the members 28 and 30 are joined at the interface proximate the vertical interface 34, the resulting radius of curvature is relatively small. Conversely, if the members 28 and 30 are joined at the interface 32, the resulting radius of curvature may be significantly larger. The radius of curvature may also be affected by other variables, such as the magnetostrictive strength of the magnetostrictive member 28, the relative cross-sectional areas of the members 28 and 30, and the stiffness of the substrate member 30. When the magnetic field B is deactivated, the magnetostrictive member 28 contracts to its original size, and the stylet 20 returns to the configuration shown in FIG. 2.

Since the stylet 20 curves in a direction dictated by the positions of the members 28 and 30 relative to one another, it is advantageous for a physician using the stylet 20 to be able to determine these relative positions. Accordingly, a handle 26 is provided at the proximal end 24 of the stylet 20, as illustrated in FIG. 2. The handle 26 is fixedly attached to the proximal end 24 of the stylet 20 so that as a physician rotates the handle 26 about the longitudinal axis of the stylet 20, the stylet 20 rotates along with the handle 26. The handle 26 advantageously includes a register that indicates the orientation of the stylet 20 to the physician during the implantation procedure. As illustrated in FIG. 2, the register may be a flattened portion 31 of the handle 26, although other shapes, such as an L-shape, or marks may be suitable as well. In this embodiment, it may be advantageous to align the flat portion 31 of the handle 26 with the stylet 20 such that the stylet curves downward when the flat portion 31 faces upward.

Figure 7:
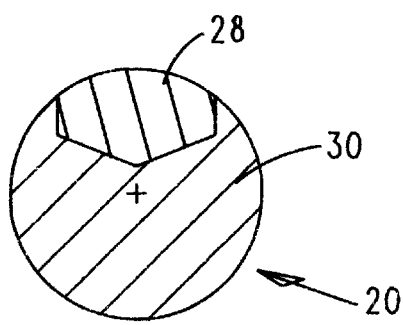
FIG. 7 is a cross-sectional view of an alternate embodiment of the stylet of FIG. 3.
Figure 8:
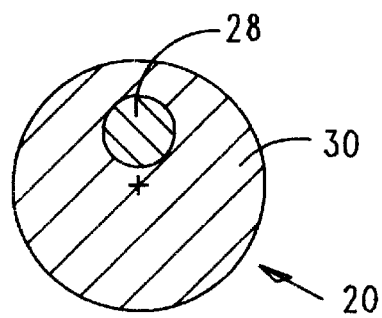
FIG. 8 is a cross-section view of another alternate embodiment of the stylet of FIG. 3.

There may be a number of different possible combinations of shapes and sizes of the members 28 and 30. FIGS. 7 and 8 are cross-sectional views of the members 28 and 30 that show just two different possible combinations of sizes and configurations. In the embodiment shown in FIG. 7, the magnetostrictive member 28 is disposed in a four-sided groove in the substrate member 30. The four-sided groove may produce a stronger interface than the one-sided interface illustrated in FIG. 4. Another structure that may provide certain advantages, such as increased strength and better biocompatibility, is shown in FIG. 8. In this embodiment, the magnetostrictive member 28 may be enclosed within the substrate member 30.

Figure 9:
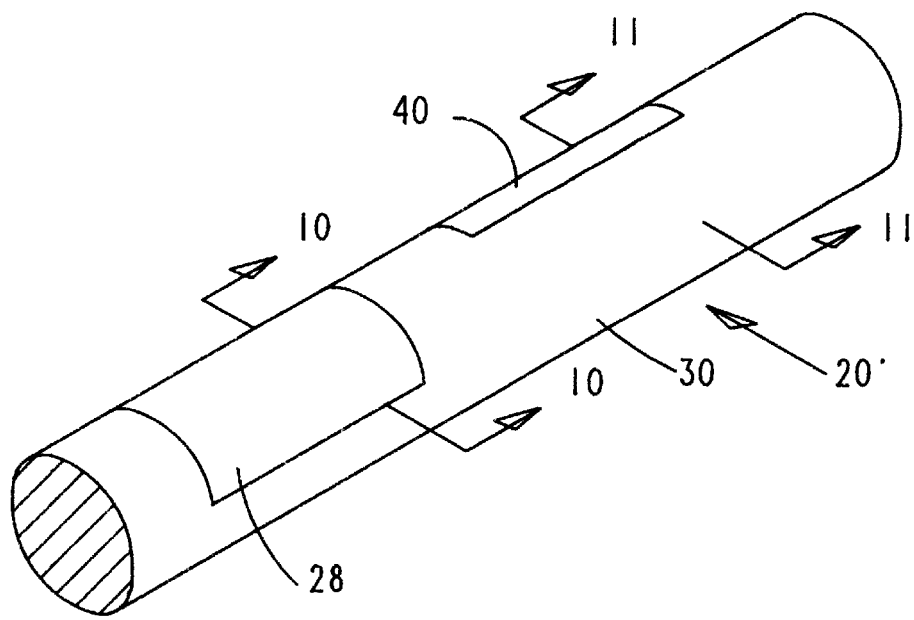
FIG. 9 is a perspective view of a portion of another embodiment of a steerable stylet in accordance with the present invention.
Figure 10:
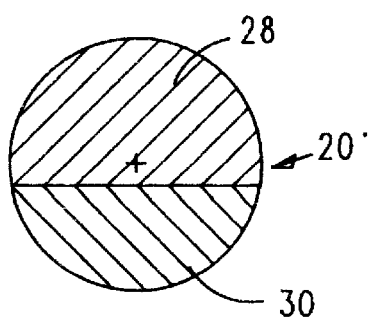
FIG. 10 is a cross-sectional view of the stylet of FIG. 9 taken at line 10—10 of FIG. 9.
Figure 11:
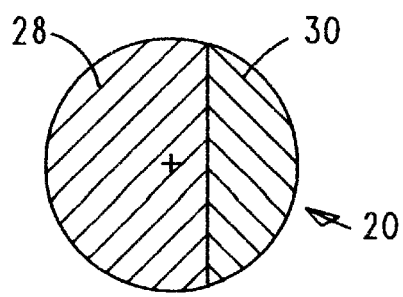
FIG. 11 is a cross-sectional view of the stylet of FIG. 9 taken at line 11—11 of FIG. 9.

FIGS. 9, 10, and 11 depict an alternate embodiment of the stylet, now designated by the reference numeral 20'. To simplify the description of this alternate embodiment, like reference numerals are used to identify structural elements similar to those in previously discussed embodiments. In this alternate embodiment, the stylet 20' incorporates two magnetostrictive members 28 and 40 positioned to introduce curves in the stylet 20' in two different directions. The magnetostrictive member 28 is disposed along one longitudinal plane of the stylet 20', and the other magnetostrictive member 40 is disposed along another longitudinal plane of the stylet 20'. As illustrated in this embodiment, the plane of the magnetostrictive member 28 is rotated at an angle of about 90 degrees relative to the plane of the magnetostrictive member 40, as clearly shown in FIGS. 10 and 11. Thus, as discussed below, the stylet 20' is capable of curving in two directions perpendicular to one another.

FIGS. 12 and 13 show, respectively, a top view and side view of the stylet 20' under the influence of the magnetic field B. In this embodiment, both of the magnetostrictive members 28 and 40 are composed of a magnetostrictive material that expands upon application of a magnetic field.

Activation of the magnetic field B causes the stylet 20' to bend simultaneously in two directions. The portion of the stylet 20' proximate the magnetostrictive member 40 bends sideways in response to the expansion of the magnetostrictive member 40. Similarly, the portion of the stylet 20' proximate the magnetostrictive member 28 bends downward in response to the expansion of the magnetostrictive 28. Of course, the number and relative longitudinal and rotational positions of the magnetostrictive members, such as the members 28 and 40, may be varied greatly to tailor the shape of the stylet 20' to the particular body passage used for in vivo insertion.

Figure 14:
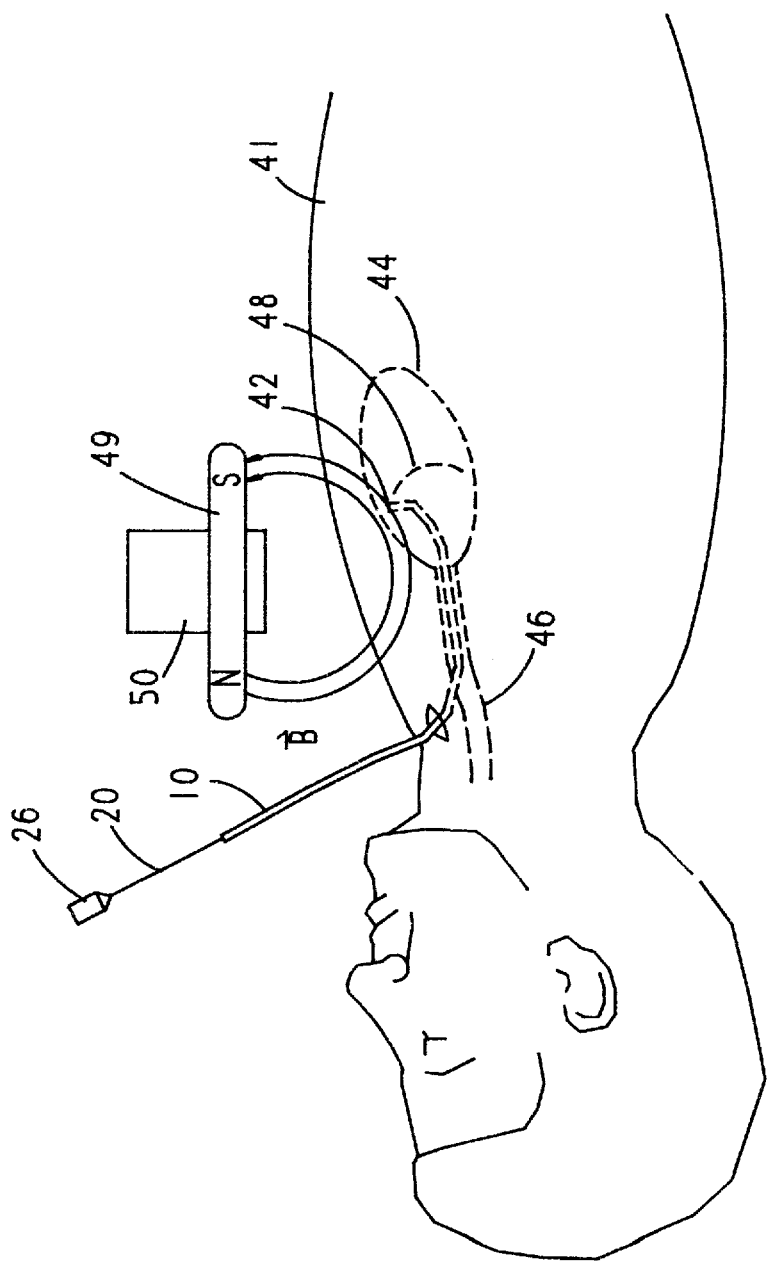
FIG. 14 is a side view of an endocardial implantation of the lead assembly using a steerable stylet in accordance with the present invention.

FIG. 14 shows a side view of a human patient 41 during implantation of the lead assembly 10 into the coronary sinus 42 (shown dashed) within the heart 44 (shown dashed). As shown in FIG. 14, the lead assembly 10 is inserted through a small incision in the body and into a body vessel, such as the jugular vein 46. The distal end 22 of the stylet 20 is shown disposed in the right atrium 48. The magnetic field B may be produced by a toroidally shaped coil 49 coupled to a fluoroscope 50. When coupled to the fluoroscope 50, the toroidally shaped coil 49 takes advantage of the convenient positioning capabilities of the fluoroscope 50. Alternatively, the toroidally shaped coil 49 may be placed directly on the body of the patient 41 and moved independently of the fluoroscope 50. Using either construction, it may be desirable to shield the magnetic field B to avoid distortion of the fluoroscopy imaging. The shielding may be accomplished using mu-metal or nickel plating, for instance.

During the insertion procedure, the stylet 20 is positioned rotationally by manipulating the handle 26 to place the distal end 22 of the stylet 20 in the proper orientation for insertion into the body or body vessel just prior to application of the magnetic field B. Upon activation of the magnetic field B, the distal end 22 of the stylet 20 assumes the proper curvature, and the physician may then advance the stylet 20 readily into the particular portion of the body or body vessel.

Figure 15:
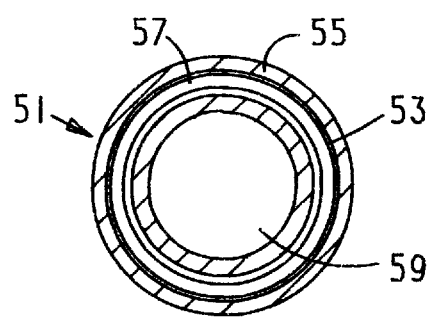
FIG. 15 is a cross-sectional view of a special lead assembly for producing a magnetic field.

Rather than using a source for the magnetic field B that is located external to the patient 41, a special lead assembly 51, shown in cross-section in FIG. 15, may be used to produce a suitable magnetic field B. The lead assembly 51 includes an inner sleeve 53 and an outer sleeve 55, both of which are advantageously made of biocompatible material, such as silicone rubber. Sandwiched between the inner sleeve 53 and the outer sleeve 55 is a highly inductive coil 57 that is wound around the inner sleeve 53. The inner sleeve 53 defines a central aperture 59 in the lead assembly 51 so that the stylet 20 may be inserted within the lead assembly 51. To cause the stylet 20 to curve, an electrical current is fed into the coil 57 to produce a magnetic field B in the axial direction of the stylet 20. Once the stylet 20 has been properly located within the patient 41, the special lead assembly 51 may be removed, and the lead assembly 10 may be positioned by disposing it on the properly positioned stylet 20. Of course, the regular lead assembly 10 may be used to produce the magnetic field B instead of the special lead assembly 51. However, most known lead assemblies, such as the lead assembly 10, have high resistance and low inductance making them generally unsuitable for producing the requisite magnetic field.

The utilization of a magnetostrictive stylet 20 may be used in a variety of in vivo implantation contexts where the peculiarities of the particular body passage or the delicacy of surrounding tissues requires careful steerage. Examples of other possible applications for the magnetically steerable stylet 20 may include intracranial placement of drug infusion catheters or shunts, insertion of subcutaneously placed supply lines for implantable infusion pumps, or in vivo placement of cryotherapeutic catheters.

Figure 16:
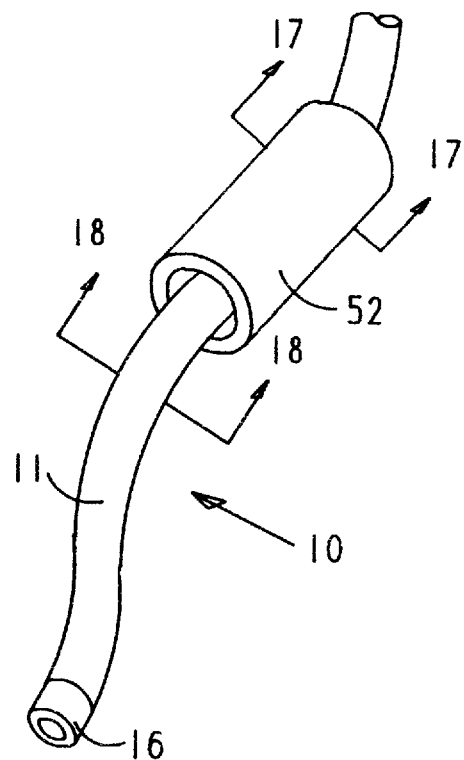
FIG. 16 is a pictorial view of an alternate embodiment of the lead assembly using a steerable stylet in accordance with the present invention.
Figure 17:
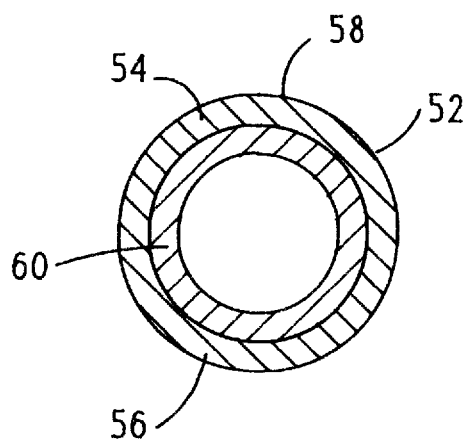
FIG. 17 is a cross-sectional view of the lead assembly of FIG. 16 taken at line 17—17 of FIG. 16.
Figure 18:
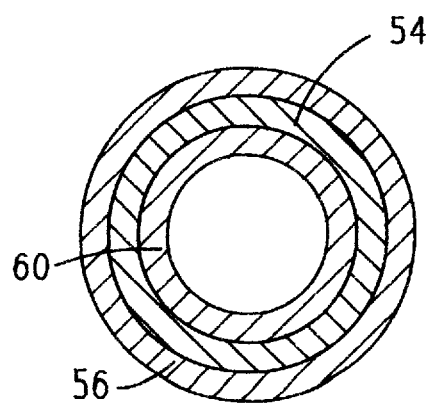
FIG. 18 is a cross-sectional view of the lead assembly of FIG. 16 taken at line 18—18 of FIG. 16.

In another alternate embodiment of the present invention shown in FIGS. 16, 17, and 18, the magnetically steerable functionality of the stylet 20 in the aforementioned embodiments is incorporated directly into the lead body 11 of the lead assembly 10. Referring first to FIGS. 16 and 17, a cylindrical sleeve 52 is disposed around the lead body 11. The sleeve 52 includes a magnetostrictive member 54 that is coupled to a substrate member 56. The members 54 and 56 are surrounded by a biocompatible jacket 58 that may be formed from the same biocompatible material used to form the exterior 60 of the lead body 11. The jacket 58 of the sleeve 52 may also be formed integral with the coating 60 of the lead body 11. Alternatively, the sleeve 52 may be bonded to the coating 60 of the sleeve 11 using a biocompatible adhesive. In addition, the magnetostrictive member 54 and the substrate member 56 may be incorporated into the jacket 60 of the sleeve 11 as shown in FIG. 18.

In operation, the sleeve 52 functions in a manner similar to the stylets 20 and 20' disclosed above, in that the magnetostrictive member 54 expands or contracts relative to the substrate member 56 in the presence of a suitable magnetic field. Also, as with any of the aforementioned embodiments, the number size and arrangement of the magnetostrictive members 54 and the substrate members 56 may be varied depending upon the particular application. Similarly, the number and spacing of individual sleeves 52 may be varied according to the requirements of the implantation.

While the invention is susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. In an implantable stylet, the improvement comprising:
   a first member; and
   a second member comprising a magnetostrictive material, wherein in the presence of a given magnetic field, the percent change in length of said second member is different than the percent change in length of said first member, further wherein said second member is fixedly coupled to said first member to cause said implantable stylet to curve under the influence of a given magnetic field.

2. The stylet of claim 1, wherein said first member is configured to receive said second member such that said second member is enclosed inside said first member.

3. The stylet of claim 1, wherein said first member is an elongated member and said second member is affixed to said first member along a longitudinal interface.

4. The stylet of claim 1, wherein said first member comprises a non-magnetic metal.

5. In an implantable stylet, the improvement comprising:
   a first member;
   a second member coupled to said first member, said second member comprising a magnetostrictive material, and a handle being fixedly coupled to one end of said stylet.

6. In an implantable stylet, the improvement comprising:
   a first elongated member;
   a second elongated member being coupled longitudinally to said first elongated member, said second elongated member comprising a magnetostrictive material, wherein said first elongated member is secured to said second elongated member such that said implantable stylet bends when disposed in a suitable magnetic field.

7. The stylet of claim 6, wherein said second elongated member undergoes a different percent change in length than said first elongated member in response to a suitable magnetic field.

8. In an implantable stylet, the improvement comprising:

a first elongated member;

a second elongated member being coupled longitudinally to said first elongated member, said second elongated member comprising a magnetostrictive material; and a third elongated member, said third elongated member being coupled longitudinally to said first elongated member, said third elongated member comprising a magnetostrictive material.

9. The stylet of claim 8, wherein said second elongated member and said third elongated member are disposed in a predetermined angular relationship relative to one another.

10. In an implantable stylet the improvement comprising:

a first elongated member;

a second elongated member being coupled longitudinally to said first elongated member, said second elongated member comprising a magnetostrictive material; and a handle being fixedly coupled to one end of said stylet.

11. A lead assembly for implantation in a patient, comprising:

a lead adapted to transmit electrical impulses;

a first member coupled to said lead; and a second member coupled to said first member, said second member comprising a magnetostrictive material.

12. The lead assembly of claim 11, wherein said first member is an elongated member and said second member is affixed to said first member along a longitudinal interface.

13. The lead assembly of claim 11, wherein said first member comprises a non-magnetic metal.

14. The lead assembly of claim 11, wherein said second member undergoes a different percent change in length than said first member in response to a suitable magnetic field.

15. The lead assembly of claim 14, wherein said lead assembly is configured to curve in response to said suitable magnetic field, the degree of curvature depending on the strength of said suitable magnetic field.

* * * * *